(12) United States Patent
Cai et al.

(10) Patent No.: US 12,318,177 B2
(45) Date of Patent: Jun. 3, 2025

(54) TERMINAL BASED ON PHOTO PLETHYSMO GRAPH PPG

(71) Applicant: HONOR DEVICE CO., LTD., Shenzhen (CN)

(72) Inventors: Xinpei Cai, Shenzhen (CN); Bingxin Liu, Shenzhen (CN); Yi Liu, Shenzhen (CN); Yinjiong Tan, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 0 days.

(21) Appl. No.: 18/043,287

(22) PCT Filed: Aug. 19, 2022

(86) PCT No.: PCT/CN2022/113524
§ 371 (c)(1),
(2) Date: Feb. 27, 2023

(87) PCT Pub. No.: WO2023/087818
PCT Pub. Date: May 25, 2023

(65) Prior Publication Data
US 2025/0072771 A1    Mar. 6, 2025

(30) Foreign Application Priority Data
Nov. 18, 2021   (CN) ......................... 202111371208.0

(51) Int. Cl.
*A61B 5/0205*    (2006.01)
*A61B 5/00*      (2006.01)
*A61B 5/024*     (2006.01)

(52) U.S. Cl.
CPC ........ *A61B 5/02416* (2013.01); *A61B 5/0205* (2013.01); *A61B 5/02438* (2013.01); *A61B 5/7225* (2013.01)

(58) Field of Classification Search
CPC .............. A61B 5/0205; A61B 5/02416; A61B 5/02438; A61B 5/7225
(Continued)

(56) References Cited

U.S. PATENT DOCUMENTS

| 8,508,223 B2 | 8/2013 | Kitane et al. |
| 10,682,082 B2 | 6/2020 | Jelfs et al. |

(Continued)

FOREIGN PATENT DOCUMENTS

| CN | 102028466 A | 4/2011 |
| CN | 107196713 A | 9/2017 |

(Continued)

*Primary Examiner* — William Hernandez
(74) *Attorney, Agent, or Firm* — Fish & Richardson P.C.

(57) ABSTRACT

Embodiments of this application provide a terminal based on photo plethysmo graph PPG. The terminal includes an LED, an AFE chip, a processor, a delay circuit, and a plurality of PDs, the first PD is configured to receive a second optical signal reflected by the skin of the user, and convert the second optical signal into a first electrical signal; the second PD is configured to receive the second optical signal reflected by the skin of the user, and convert the second optical signal into a second electrical signal; the delay circuit is configured to perform delay processing on the first electrical signal; the AFE chip is configured to determine a target signal based on the second electrical signal and the first electrical signal subjected to the delay processing; and the processor is configured to process the target signal to obtain a health status of the user.

10 Claims, 13 Drawing Sheets

(58) Field of Classification Search
USPC .......................................... 324/71.1; 356/41
See application file for complete search history.

(56) References Cited

U.S. PATENT DOCUMENTS

| | | | | |
|---|---|---|---|---|
| 2007/0142715 | A1* | 6/2007 | Banet | A61B 5/14552 |
| | | | | 600/323 |
| 2010/0324387 | A1* | 12/2010 | Moon | A61B 5/02125 |
| | | | | 600/324 |
| 2014/0107493 | A1 | 4/2014 | Yuen et al. | |
| 2015/0223708 | A1* | 8/2015 | Richards | A61B 5/0205 |
| | | | | 600/479 |
| 2016/0324477 | A1* | 11/2016 | Gunturi | A61B 5/721 |
| 2016/0360986 | A1* | 12/2016 | Lange | A61B 5/6824 |
| 2017/0055860 | A1* | 3/2017 | Vermeulen | A61B 5/02433 |
| 2018/0085058 | A1* | 3/2018 | Chakravarthi | G16H 40/67 |
| 2018/0116604 | A1 | 5/2018 | Newberry | |
| 2018/0360374 | A1 | 12/2018 | Martikka et al. | |
| 2019/0282179 | A1 | 9/2019 | Newberry | |
| 2023/0120967 | A1* | 4/2023 | Wang | A61B 5/02427 |
| | | | | 368/11 |
| 2023/0320604 | A1* | 10/2023 | Cai | A61B 5/681 |
| | | | | 600/479 |
| 2024/0324955 | A1* | 10/2024 | Tan | A61B 5/02433 |
| 2024/0358292 | A1* | 10/2024 | Kumar | A61B 5/02427 |

FOREIGN PATENT DOCUMENTS

| | | |
|---|---|---|
| CN | 107735019 A | 2/2018 |
| CN | 110269618 A | 9/2019 |
| CN | 210784331 U | 6/2020 |
| CN | 112043055 A | 12/2020 |
| CN | 112650707 A | 4/2021 |
| CN | 113543294 A | 10/2021 |

* cited by examiner

TERMINAL BASED ON PHOTO PLETHYSMO GRAPH PPG

CROSS-REFERENCE TO RELATED APPLICATIONS

This application is a national stage of International Application No. PCT/CN2022/113524, filed on Aug. 19, 2022, which claims priority to Chinese Patent Application No. 202111371208.0, filed on Nov. 18, 2021. The disclosures of both of the aforementioned applications are hereby incorporated by reference in their entireties.

TECHNICAL FIELD

This application relates to the field of terminal technologies, and in particular, to a terminal based on photo plethysmo graph PPG.

BACKGROUND

Generally, a terminal may measure human heart rate, blood oxygen, respiratory rate and other parameters by using photo plethysmo graph (photo plethysmo graph. PPG), so as to obtain a human health status. The method may be implemented by a photo diode (photo diode, PD) and a light emitting diode (light emitting diode, LED) in the terminal. Specifically, the PD receives an optical signal emitted by the LED and reflected by skin of a user, and converts the optical signal into an electrical signal; and then the terminal analyzes the electrical signal to obtain the health status of the user.

However, accuracy of collection through a current PPG signal channel is not high. For example, in a sports scenario, there may be a situation in which the PD cannot be in full contact with the skin, resulting in poor quality of a signal collected by the PD, which affects accuracy of the health status of the user obtained by analyzing and processing the signal, thereby affecting user experience.

SUMMARY

Embodiments of this application provide a terminal based on photo plethysmo graph (PPG). The terminal may be based on a plurality of PDs and a delay circuit, so that a target signal with good quality can be obtained, and accurate human health status may be obtained based on the target signal.

According to a first aspect, an embodiment of this application provides a terminal based on photo plethysmo graph PPG. The terminal includes a light emitting diode LED, an analog front end AFE chip, a processor, and a plurality of photo diodes PDs, where the plurality of PDs include a first PD and a second PD, the first PD and the second PD are connected to the AFE chip in parallel, and the AFE chip is connected to the processor; the LED is configured to emit a first optical signal to skin of a user; the first PD is configured to receive a second optical signal reflected by the skin of the user, and convert the second optical signal into a first electrical signal; and the second PD is configured to receive the second optical signal reflected by the skin of the user, and convert the second optical signal into a second electrical signal; the terminal further includes a delay circuit, and the delay circuit is connected in series in a branch where the first PD is located; the delay circuit is configured to perform delay processing on the first electrical signal, the AFE chip is configured to determine a target signal based on the second electrical signal and the first electrical signal subjected to the delay processing; and the processor is configured to process the target signal to obtain a health status of the user.

In this way, the terminal may perform, based on the delay circuit, delay processing on the first electrical signal converted by the first PD, so that the AFE chip may obtain a first electrical signal and a second electrical signal independent of each other, where the first electrical signal and the second electrical signal are obtained based on the first optical signal emitted by the LED at the same time and reflected by the skin of the user, so that the AFE chip can select to obtain the target signal with high accuracy, and then the processor processes the target signal to obtain the health status of the user.

In a possible implementation, the delay circuit includes an RC filter and a controllable switching transistor, and the RC filter includes a resistor and a capacitor; a control end of the controllable switching transistor is connected to a first end of the resistor and a first end of the capacitor, a first end of the controllable switching transistor is connected to the first PD, a second end of the controllable switching transistor is connected to an input end of the AFE chip, a second end of the resistor is connected to a general-purpose interface of the AFE chip, and a second end of the capacitor is grounded; the RC filter is configured to control voltage at the control end of the controllable switching transistor; and the controllable switching transistor is configured to turn on when the voltage at the control end is higher than a preset threshold, so as to perform delay processing on the first electrical signal.

In this way, the terminal may control delay time of the delay circuit through the RC filter. The RC filter is configured to allow the voltage at the control end of the controllable switching transistor to reach the preset threshold after a preset time. The controllable switching transistor is turned on when the voltage at the control end of the controllable switching transistor is higher than the preset threshold, so as to implement the delay processing of the first electrical signal.

In a possible implementation, the delay circuit includes a timer and a controllable switching transistor; a control end of the controllable switching transistor is connected to an output end of the timer, a first end of the controllable switching transistor is connected to the first PD, and a second end of the controllable switching transistor is connected to an input end of the AFE chip; and the timer is configured to delay the first electrical signal output to the control end of the controllable switching transistor for a preset time compared with the second electrical signal.

In this way, the terminal may control delay time of the delay circuit through the timer. After the timer controls the preset time, the controllable switching transistor is turned on, and the AFE chip obtains the first electrical signal after the preset time, so as to implement the delay processing of the first electrical signal.

In a possible implementation, the delay circuit includes a power management chip; the power management chip includes a signal input pin, a signal output pin, and a power input pin, where the power input pin is configured to connect to a direct current voltage, and the power management chip is connected to the first PD in series through the signal input pin and the signal output pin; and the power management chip is configured to generate, by using the direct current voltage, a first electrical signal delayed for a preset time compared with the second electrical signal.

In this way, the power management chip may generate the first electrical signal delayed for the preset time based on the preset time and the input direct current voltage, so as to implement the delay processing of the first electrical signal.

In a possible implementation, the plurality of PDs are eight PDs, the first electrical signal is four electrical signals generated by four of the eight PDs, and the AFE chip has four signal receiving channels.

In this way, the AFE chip with four signal receiving channels may obtain, through the delay circuit, eight electrical signals after delay processing of four electrical signals of eight electrical signals obtained by the eight PDs, and two signals obtained by the same channel may be separated through the delay processing. The AFE chip may obtain eight independent electrical signals through the four signal receiving channels.

In a possible implementation, the plurality of PDs are twelve PDs, the first PD includes four first sub-PDs and four second sub-PDs, and the first sub-PDs and the second sub-PDs are connected to the AFE chip in parallel; the first sub-PDs are configured to receive a second optical signal reflected by the skin of the user, and convert the second optical signal into a first sub-electrical signal; the second sub-PDs are configured to receive the second optical signal reflected by the skin of the user, and convert the second optical signal into a second sub-electrical signal; the delay circuit includes a first delay circuit and a second delay circuit, the first delay circuit and the second delay circuit have different delay time, the first delay circuit is connected in series in a branch where the first sub-PDs are located, and the second delay circuit is connected in series in a branch where the second sub-PDs are located; the first delay circuit is configured to perform delay processing on the first sub-electrical signal; and the second delay circuit is configured to perform delay processing on the second sub-electrical signal.

In this way, the AFE chip with four signal receiving channels may obtain, through the first delay circuit and the second delay circuit, twelve electrical signals after delay processing of eight electrical signals of twelve electrical signals obtained by the twelve PDs. The eight electrical signals subjected to delay processing include four first sub-electrical signals subjected to first delay processing and four second sub-electrical signals subjected to second delay processing. Each signal receiving channel of the AFE chip may obtain, through the first delay circuit and the second delay circuit, three electrical signals, and the three electrical signals are delayed by the first delay circuit and the second delay circuit for different time, so that three independent electrical signals can be obtained. The AFE chip may obtain twelve independent electrical signals through the four signal receiving channels.

In a possible implementation, the plurality of PDs are annularly distributed.

In this way, the plurality of PDs may be located on the terminal through annular distribution, and when a user is in contact with the terminal at any angle, the user is in contact with one of the PDs. When any one of the PDs is in contact with skin of the user, an electrical signal with high signal quality may be obtained, so as to obtain accurate a human health status.

In a possible implementation, the health status of the user includes at least one of heart rate, oxygen saturation, and respiratory rate of the user.

In this way, the terminal may be used to obtain any one of parameters of heart rate, oxygen saturation, and respiratory rate of the user, and may also obtain any two or all of the foregoing parameters at the same time, so that the user may obtain the health status of the user based on the terminal.

In a possible implementation, the terminal is a wearable device.

In this way, the user may monitor the health status in various scenarios through the terminal.

In a possible implementation, the first optical signal is at least one of a red light signal, a green light signal, and an infrared light signal.

In this way, the terminal may control an emitting color of the LED based on different application scenarios.

According to a second aspect, an embodiment of this application provides a control method based on photo plethysmo graph PPG, applied to the wearable device according to any one of the implementations of the first aspects. The method includes: obtaining, through a first PD, a second optical signal reflected by skin of a user, and converting the second optical signal into a first electrical signal, where the second optical signal is obtained after the first optical signal emitted by an LED is reflected by the skin; obtaining, through a second PD, a second optical signal reflected by the skin of the user, and converting the second optical signal into a second electrical signal; performing delay processing on the first electrical signal through a delay circuit; determining a target signal based on the second electrical signal and the first electrical signal subjected to the delay processing; and processing the target signal to obtain a health status of the user.

In a possible implementation, the performing delay processing on the first electrical signal through a delay circuit includes: controlling, by an RC filter, voltage at a control end of a controllable switching transistor; where the controllable switching transistor is turned on when the voltage at the control end is higher than a preset threshold, so as to implement the delay processing of the first electrical signal.

In a possible implementation, the performing delay processing on the first electrical signal through a delay circuit includes: delaying, by a timer, the first electrical signal output to the control end of the controllable switching transistor for a preset time compared with the second electrical signal.

In a possible implementation, the performing delay processing on the first electrical signal through a delay circuit includes: generating, by a power management chip, a first electrical signal delayed for a preset time compared with the second electrical signal by using a direct current voltage.

In a possible implementation, the plurality of PDs are eight PDs, the first electrical signal is four electrical signals generated by four of the eight PDs, and the AFE chip has four signal receiving channels.

In a possible implementation, the plurality of PDs are twelve PDs, the first PD includes four first sub-PDs and four second sub-PDs, and the AFE chip has four signal receiving channels; the obtaining, through a first PD, a second optical signal reflected by skin of a user includes: obtaining the second optical signal reflected by the skin of the user through eight first PDs; the obtaining, through a second PD, a second optical signal reflected by the skin of the user includes: obtaining the second optical signal reflected by the skin of the user through four second PDs; and the performing delay processing on the first electrical signal through a delay circuit includes: performing delay processing on four first sub-electrical signals through a first delay circuit, and performing delay processing on another four second sub-electrical signals through a second delay circuit.

In a possible implementation, the plurality of PDs are annularly distributed.

In a possible implementation, the health status of the user includes at least one of heart rate, oxygen saturation, and respiratory rate of the user.

In a possible implementation, the method is applied to a wearable device.

In a possible implementation, the first optical signal is at least one of a red light signal, a green light signal, and an infrared light signal.

According to a third aspect, an embodiment of this application provides a computer-readable storage medium. The computer-readable storage medium stores instructions, and the instructions, when executed, enable a computer to perform the control method according to any one of the second aspect or the implementations of the second aspect.

According to a fourth aspect, an embodiment of this application provides a computer program product, including a computer program. The computer program, when run, enables a computer to perform the control method according to any one of the second aspect or the implementations of the second aspect.

It should be understood that the technical solutions according to the second aspect to the fourth aspect of this application correspond to the technical solution according to the first aspect of this application, and beneficial effects achieved by the aspects and corresponding feasible implementations are similar. Details are not described herein again.

DESCRIPTION OF EMBODIMENTS

To clearly describe the technical solutions in embodiments of this application, in embodiments of this application, words such as "first" and "second" are used to distinguish between same items or similar items with basically the same functions and effects. For example, a first value and a second value are merely used to distinguish between different values, but not limit a sequence thereof. A person skilled in the art may understand that words such as "first" and "second" do not limit a quantity or an execution order, and the words such as "first" and "second" do not necessarily indicate a difference.

It should be noted that, in this application, words such as "for example" or "such as" are used to indicate an example, illustration, or description. Any embodiment or design solution described as "for example" or "such as" in this application should not be construed as being preferred or advantageous over other embodiments or design solutions. To be precise, the use of the words such as "example" or "for example" is intended to present a related concept in a specific manner.

In this application, "at least one" means one or more, and "a plurality of" means two or more. "And/or" describes an association relationship between associated objects, and indicates that three relationships may exist. For example, A and/or B may indicate the following cases: Only A exists, both A and B exist, and only B exists, where A and/or B may indicate a singular or plural form. The symbol "/" usually indicates an "or" relationship between the associated objects. "At least one of the following items" or other similar expressions represent any combination of these items, including any combination of a singular or a plural. For example, at least one of a, b, or c may represent a, b, c, a-b, a-c, b-c, or a-b-c, where a, b, and c may be singular or plural.

With the increasing demand of users, terminals may provide more functions. For example, to meet the demand of users for monitoring their own health statuses, terminals may monitor the health statuses of the users.

Figure 1:
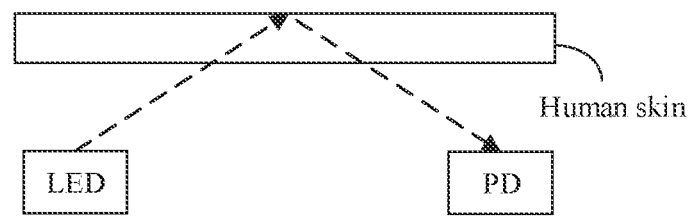
FIG. 1 is a schematic diagram of a PPG principle according to an embodiment of this application.

A terminal may measure parameters such as human heart rate, blood oxygen, and respiratory rate by using photo plethysmo graph (photo plethysmo graph, PPG), so as to obtain a human health status. A specific principle is shown in FIG. 1. An LED emits a light beam of a wavelength to irradiate skin surface, and the light beam is received by PDs through transmission or reflection, and the PDs convert optical signals into electrical signals. Therefore, the terminal may obtain the electrical signals including a human health status through the PDs, and then analyze and process the electrical signals to obtain the human health status. The absorption of light by human muscles, bones, veins, and the like is essentially unchanged without substantial movement, while blood is flowing, so that the absorption of light changes. Therefore, when the PDs convert optical signals into electrical signals, because the absorption of light by arteries changes, while the absorption of light by other human tissues is essentially unchanged, the terminal may divide the obtained electrical signals into alternating current (alternating current, AC) signals and direct current (direct current, DC) signals, and extract the AC signals to obtain a health status of a user.

The terminal may be a portable terminal such as a smartwatch or a smart band, and the LED and the PDs may be mounted in a rear cover of the portable terminal. The LED emits optical signals, and the PDs receive optical signals reflected by human % wrist skin, and convert the optical signals into electrical signals. Therefore, the terminal may obtain, through the PDs, electrical signals representing a human health status, and process the electrical signals to obtain the human health status.

In some cases, for example, in a sports scenario, the PDs cannot be in full contact with the skin due to unstable contact between the rear cover of the watch and the skin, resulting in poor quality of the electrical signals collected by the PDs. Therefore, a plurality of PDs may be added, and electrical signals collected by the added PDs are combined with the electrical signals collected by the original PDs. For example, the terminal includes four PDs, which are denoted as PD1 to PD4, and four PDs are added, which are denoted as PD5 to PD8. An electrical signal collected by the PD1 is combined with an electrical signal collected by the PD5 by connecting the PD1 to the PD5. Similarly, an electrical signal collected by the PD2 is combined with an electrical signal collected by the PD6, an electrical signal collected by the PD3 is combined with an electrical signal collected by the PD7, and an electrical signal collected by the PD4 is combined with an electrical signal collected by the PD8, so that the PDs can output four combined signals.

However, when there is a poor signal in the PDs, the poor signal is superimposed with other signals, which affects the quality of a composite signal and leads to further deterioration of signal quality.

In view of this, an embodiment of this application provides a terminal based on PPG. The terminal includes a light emitting diode LED, an analog front end AFE chip, a processor, a delay circuit, and a plurality of photo diodes PDs, where the plurality of PDs include a first PD and a second PD, the first PD and the second PD are connected to the AFE chip in parallel, the AFE chip is connected to the processor, and the delay circuit is connected in series in a branch where the first PD is located.

Specifically, the LED is configured to emit a first optical signal to skin of a user; the first PD is configured to receive a second optical signal reflected by the skin of the user, and convert the second optical signal into a first electrical signal; the second PD is configured to receive the second optical signal reflected by the skin of the user, and convert the second optical signal into a second electrical signal; the delay circuit is configured to perform delay processing on the first electrical signal; the AFE chip is configured to determine a target signal based on the second electrical signal and the first electrical signal subjected to the delay processing; and the processor is configured to process the target signal to obtain a health status of the user.

The AFE chip may obtain, through the delay circuit, a first electrical signal and a second electrical signal subjected to delay processing, and the first electrical signal and the second electrical signal are independent of each other. The AFE chip may select the first electrical signal and the second electrical signal to obtain a target signal with better signal quality, and then the processor analyzes and processes the target signal to obtain the human health status. The delay processing of the first electrical signal through the delay circuit enables multiple electrical signals collected by the plurality of PDs to be independently received by the AFE chip, so that the AFE chip can select independently, based on the electrical signals collected by the PDs, to obtain target signals, so as to comprehensively extract target signals, and avoid interference caused by signal superposition.

Figure 2:
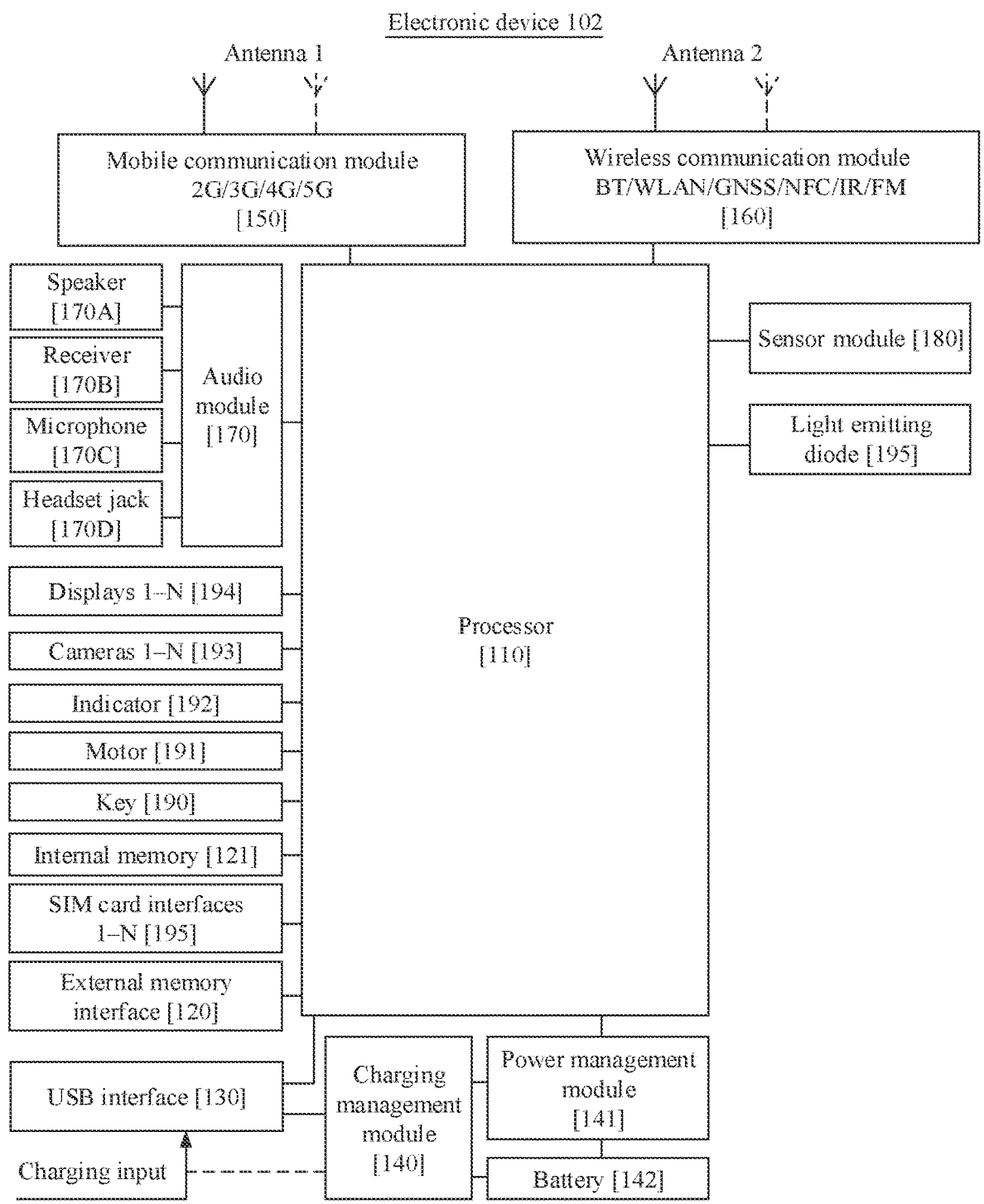
FIG. 2 is a schematic diagram of a structure of a terminal according to an embodiment of this application.

In this embodiment, a structure of the terminal may be shown in FIG. 2. FIG. 2 is a schematic diagram of the structure of the terminal according to an embodiment of this application. The terminal may include a processor 110, an external memory interface 120, an internal memory 121, a universal serial bus (universal serial bus, USB) interface 130, an antenna 1, an antenna 2, a mobile communication module 150, a wireless communication module 160, a sensor module 180, a key 190, a motor 191, an indicator 192, a camera 193, a display 194, a subscriber identification module (subscriber identification module, SIM) card interface 195, a light emitting diode 196, and the like. The sensor module 180 may include a photo diode. Positions in which the photo diode and the light emitting diode are deployed may be as shown in FIG. 3.

It may be understood that the structure illustrated in this embodiment does not constitute a specific limitation on the terminal. In some other embodiments, the terminal may include more or fewer components than those illustrated, or combine some components, or split some components, or have different component arrangements. The illustrated components may be implemented by hardware, software, or a combination of software and hardware.

An architecture of the terminal has been briefly described above. In the following descriptions, that the terminal is a smartwatch among wearable devices is used as an example to describe a connection mode in the terminal according to an embodiment of this application in detail.

Figure 3:
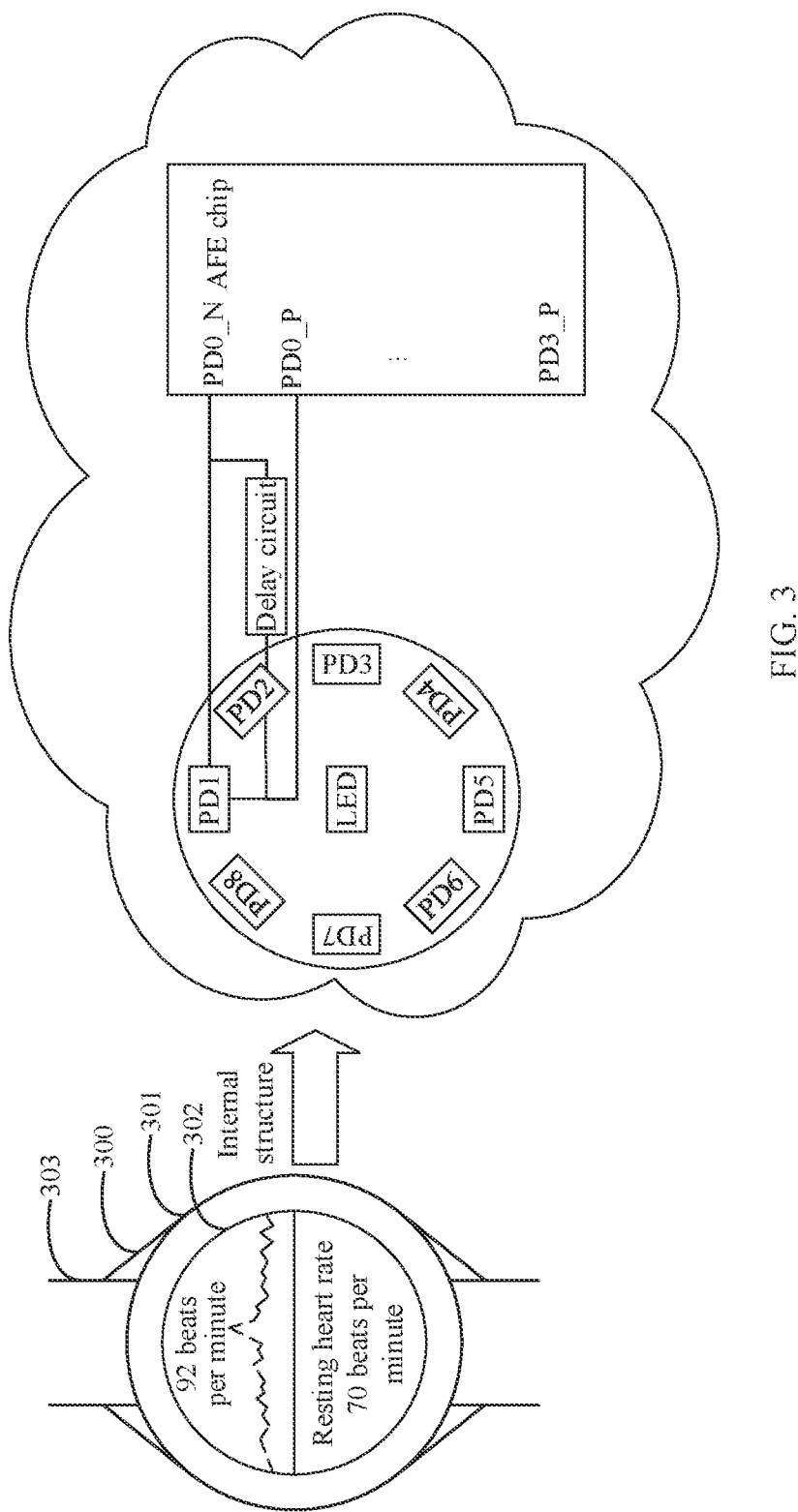
FIG. 3 is a schematic diagram of an interface and a connection relationship of a smartwatch according to an embodiment of this application.

The terminal according to an embodiment of this application may be as shown in FIG. 3, and eight PDs may form an annular structure. Therefore, in a sports scenario, a user may be in full contact with one of the PDs when the user is in close contact with a rear cover of the smartwatch at any angle, so that a signal with good quality can be obtained.

Generally, the analog front end (analog front end, AFE) chip used to process signals collected by the PDs has four receiving units (receiving unit, RX), so that the AFE chip can only receive four PD signals collected at the same time. When a quantity of the PDs is more than 4, the terminal may connect the plurality of PDs in parallel, that is, superimpose collected PD signals, so that the AFE chip can receive, through the four receiving units, signals collected by the more than four PDs. For example, when the terminal has eight PDs, the terminal superimposes eight PD signals collected by the eight PDs in pairs, and obtains four superimposed signals through the receiving units of the AFE chip. However, in this way, the signals obtained by the terminal through the four receiving units of the AFE chip are superimposed signals. When one of the PDs is unstable, noise in the signal collected by the PD is superimposed in a composite signal of the signal and signals collected by other PDs, which affects the quality of signals collected by the PDs.

To obtain more PD signals, the terminal needs more PDs to collect signals, and needs to enable the AFE chip to receive independent multiple signals, so as to eliminate coupling effect of the plurality of PDs connected in parallel. The terminal may add a delay circuit to the superimposed multiple PDs connected in parallel without changing the AFE chip. With the delay circuit, the terminal splits a plurality of PD signals collected at the same time into signals at different time, and obtain the signals through the receiving units of the AFE chip.

Figure 4:
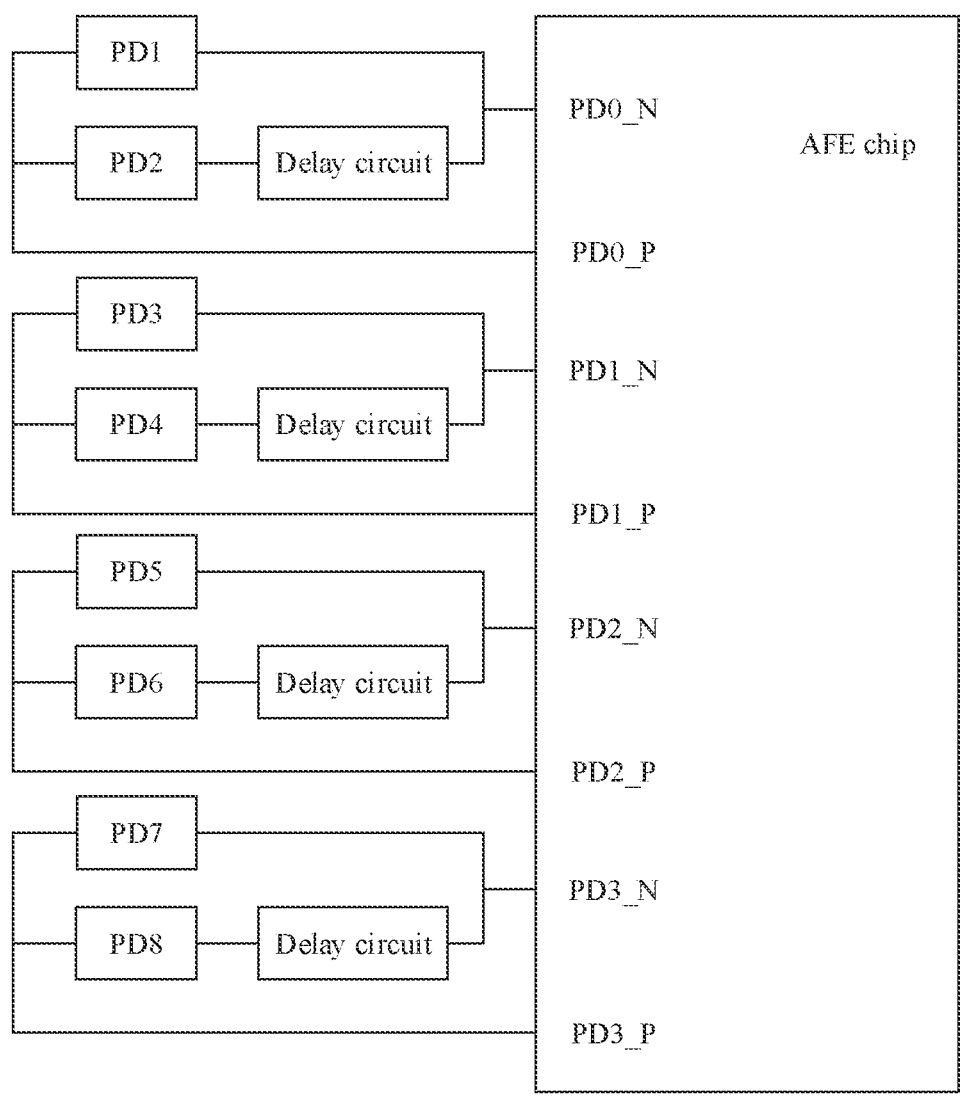
FIG. 4 is a schematic diagram of a structure of a PD connection according to an embodiment of this application.

FIG. 4 shows a signal receiving scheme according to an embodiment of this application, where eight PDs are arranged as shown in FIG. 3. FIG. 3 shows an example of application of this embodiment of this application to a smartwatch 300. 301 indicates a dial part of the watch; the inner rear of the dial includes an LED and a PD; 302 indicates a display interface of the watch, which is used to display a human health status; and 303 indicates another part of the smartwatch, such as a watch band.

As shown in FIG. 4, the PD1 and the PD2 are connected in parallel to a first receiving unit RX0 (PD0) of the AFE chip, the PD3 and the PD4 are connected in parallel to a second receiving unit RX1 (PD1) of the AFE chip, the PD5 and the PD6 are connected in parallel to a third receiving unit RX2 (PD2) of the AFE chip, and the PD7 and the PD8 are connected in parallel to a fourth receiving unit RX3 (PD3) of the AFE chip. A delay circuit is introduced respectively into a branch where the PD2 is located, a branch where the PD4 is located, a branch where the PD6 is located, and a branch where the PD8 is located. Therefore, the AFE chip may receive signals of the PD1, the PD3, the PD5, the PD7, the PD2, the PD4, the PD6, and the PD8, respectively. When the LED emits light at t0 to t1, the delay circuit has a delay time of T, where T is greater than (t1−t0). The AFE chip receives PD signals received by the PD1, the PD3, the PD5 and the PD7 through the four receiving units at t0 to t1, and receives signals of the PD2, the PD4, the PD6, and the PD8 through the four receiving units at (t1+T) to (t1+T). The signals received by the AFE chip at (t0+T) to (t1+T) are signals synchronously collected by the PD2, the PD4, the PD6, and the PD8 when the LED emits light at t0 to t1. The signals collected at t0 to t1 are delayed, through the delay circuit, for T, and received by the AFE chip at (t0+T) to (t1+T).

Figure 5:
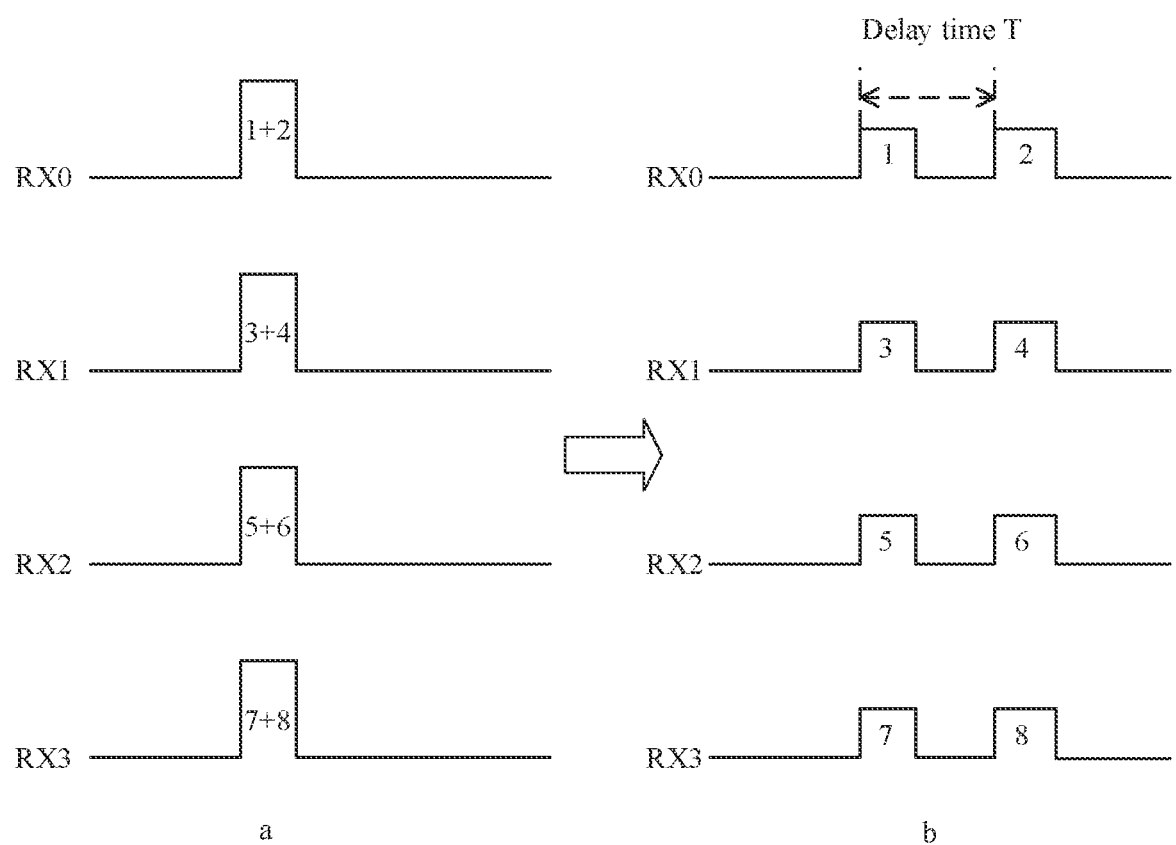
FIG. 5 is a schematic diagram showing a process of receiving a signal by a receiving unit according to an embodiment of this application.

When no delay circuit is added to the foregoing circuit, the RX0 receives a composite signal of the PD1 and the PD2 at t0 to t1, the RX1 receives a composite signal of the PD3 and the PD4 at t0 to t1, the RX2 receives a composite signal of the PD5 and the PD6 at t0 to t1, and the RX3 receives a composite signal of the PD7 and the PD8 at t0 to t1, as shown in a in FIG. 5. After a delay circuit that delays for time T is added respectively to the branch where the PD2 is located, the branch where the PD4 is located, the branch where the PD6 is located, and the branch where the PD8 is located, the RX0 receives a signal of the PD1 at t0 to t1, and receives a signal of the PD2 at (t0+T) to (t1+T); the RX1 receives a signal of the PD3 at t0 to t1, and receives a signal of the PD4 at (t0+T) to (t1+T); the RX2 receives a signal of the PD5 at t0 to t1, and receives a signal of the PD6 at (t0+T) to (t1+T); and the RX3 receives a signal of the PD7 at t0 to t1, and receives a signal of the PD8 at (t0+T) to (t1+T), as shown in b in FIG. 5. Therefore, the AFE chip may collect eight PD signals independently, so as to send the eight independent signals into a first input first output (first input first output, FIFO), and then evaluate the quality of the eight signals based on a channel selection algorithm, so as to obtain a target signal representing a health status of the user.

When evaluating the quality of PD signals, the channel selection algorithm usually requires that the DC signal amplitude of the signals is at a μA level, and the AD signal amplitude is about 0.5% to 2% of the DC signal amplitude. In addition, the signals are required to be free from obvious amplitude fluctuation and signal burr. Frequency domain energy is concentrated at 0.5 Hz to 4 Hz, so that a signal with good signal quality may be obtained to obtain index data that can reflect the health of the user.

In some possible implementations, the LED in this application may emit light of various colors, such as red light, green light or infrared light, and therefore the first optical signal is a red light signal, a green light signal, or an infrared light signal. The LED may also include a plurality of LED subunits to emit red light and green light, or red light and infrared light, or green light and infrared light at the same time, or that may emit red light, green light, and infrared light at the same time.

In addition, when analyzing the target signal, the processor may obtain heart rate, oxygen saturation, or respiratory rate that indicates the health status of the user, and the processor may also obtain heart rate and oxygen saturation, or heart rate and respiratory rate, or oxygen saturation or respiratory rate of the user for analysis of the target signal. Further, based on the absorption of different light by different human parts, different colors of light may correspond to different parameters indicating a health status of the user. For example, red light corresponds to heart rate of the user, green light corresponds to oxygen saturation of the user, and infrared light corresponds to respiratory rate of the user.

Figure 6:
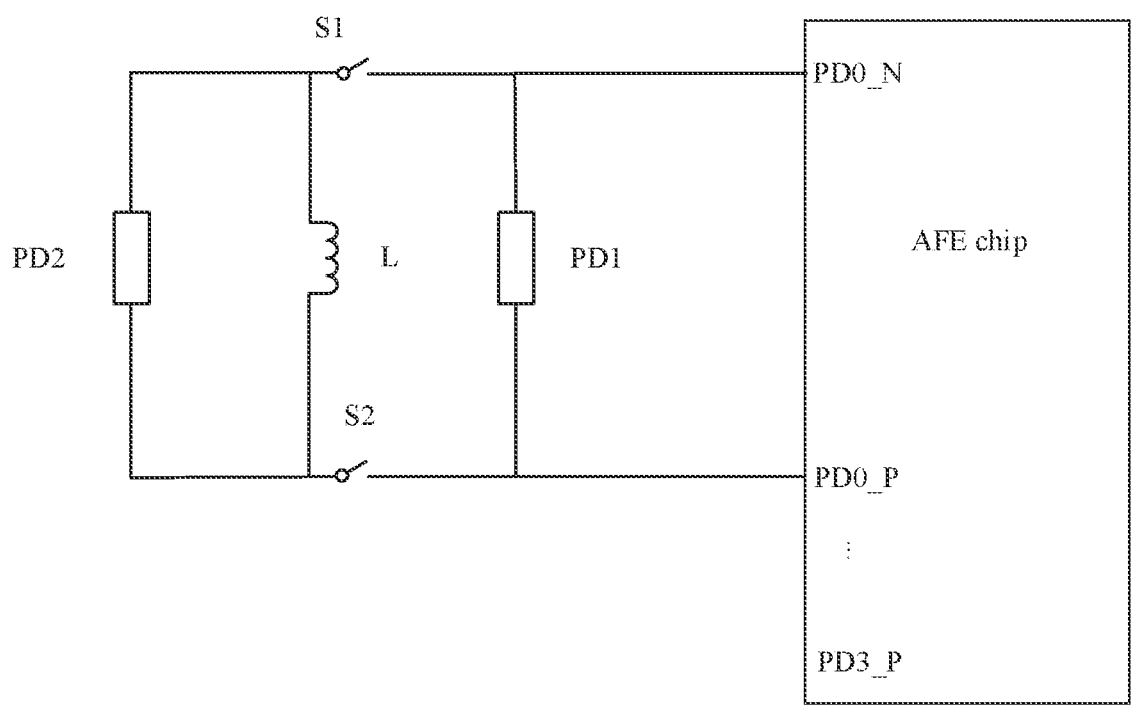
FIG. 6 is a schematic diagram of a structure of a delay circuit according to an embodiment of this application.

FIG. 6 is a schematic diagram showing energy storage of a delay circuit by using the PD1 and the PD2 as an example. In some possible implementations, energy storage of the electrical signal output by the PD2 may be implemented by an inductor and switches. When the LED emits light at t0 to t1, S1 and S2 are turned off. At this time, current from the PD1 is received by the AFE chip, and current from the PD2 is stored by an inductor L. After time T, the LED is turned off (T>(t1−t0)). S1 and S2 are turned on, and energy released by the inductor is received by the AFE chip. The energy is the current of the PD2 when the LED emits light at t0 to t1 so that the AFE chip can obtain an independent PD2 signal after time T. Because the signal of the PD2 obtained by the AFE chip after time T is the signal received when the LED emits light, the light emitting time of the LED is not changed, with little additional power consumption of a PPG device. With this circuit, an energy storage function of the PD2 in the delay circuit may be implemented. Energy released by the PD2 is received and stored by the inductor. When the switches are turned on, the inductor releases the energy to enable the AFE chip to receive the energy, so as to perform delay processing on the electrical signal.

The delay time T of the delay circuit is longer than the lighting time (t1−t0) of the LED. For example, if the AFE chip has a sampling period of 100 hertz (Hz), the AFE chip obtains a signal in the next period at an interval of 10 milliseconds (ms), the AFE chip has a sampling interval of 10 ms, and the light emitting time (t1−t0) of the LED is 79 microseconds (μs). Therefore, the delay time T needs to meet the following requirement: lighting time<T<sampling interval, that is, 79 μs<T<10 ms.

Figure 7:
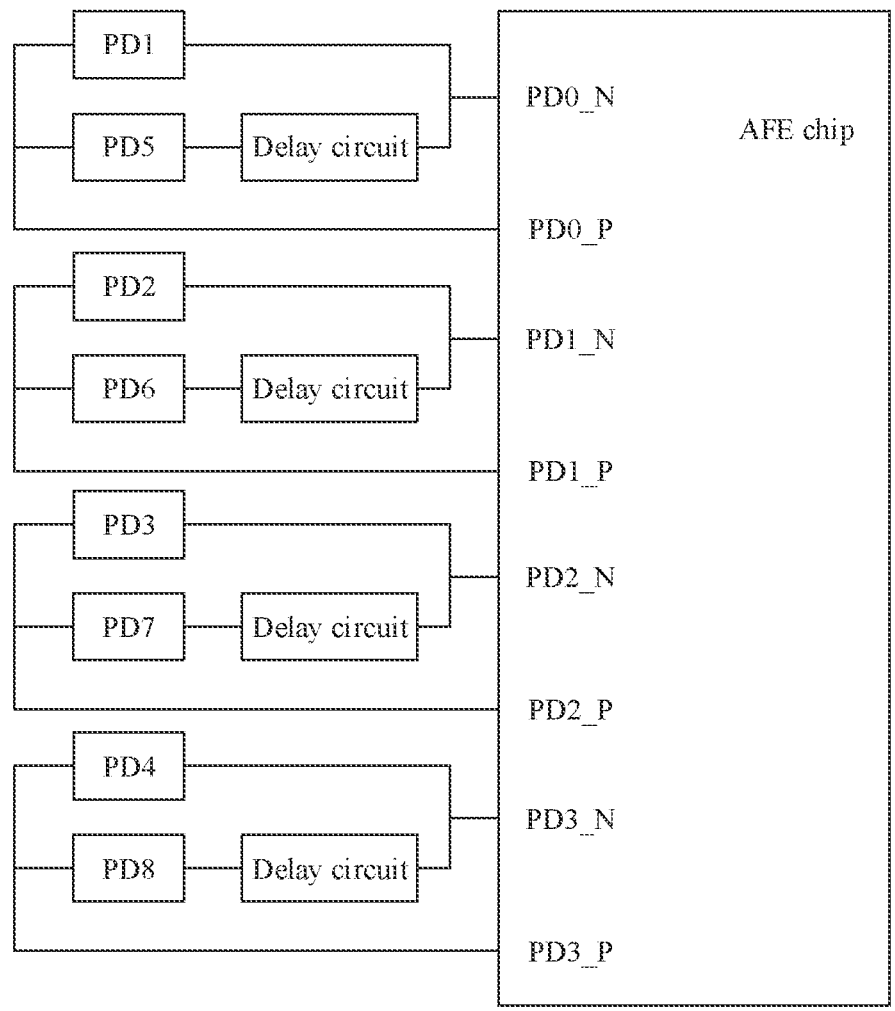
FIG. 7 is a schematic diagram of a structure of another PD connection according to an embodiment of this application.

It should be noted that when there are eight PDs and the AFE chip has four receiving units, this application is not limited to the parallel connection of the PD1 and the PD2, the PD3 and the PD4, the PD5 and the PD6, and the PD7 and the PD8, as shown in FIG. 4. Because of the technical solutions provided in this application, the AFE chip may independently receive the signal sent by each PD. Therefore, the plurality of PDs in this application may be connected in parallel in pairs, such as the PD1 and the PD5, the PD2 and the PD6, the PD3 and the PD7, and the PD4 and the PD8, as shown in FIG. 7.

Figure 8:
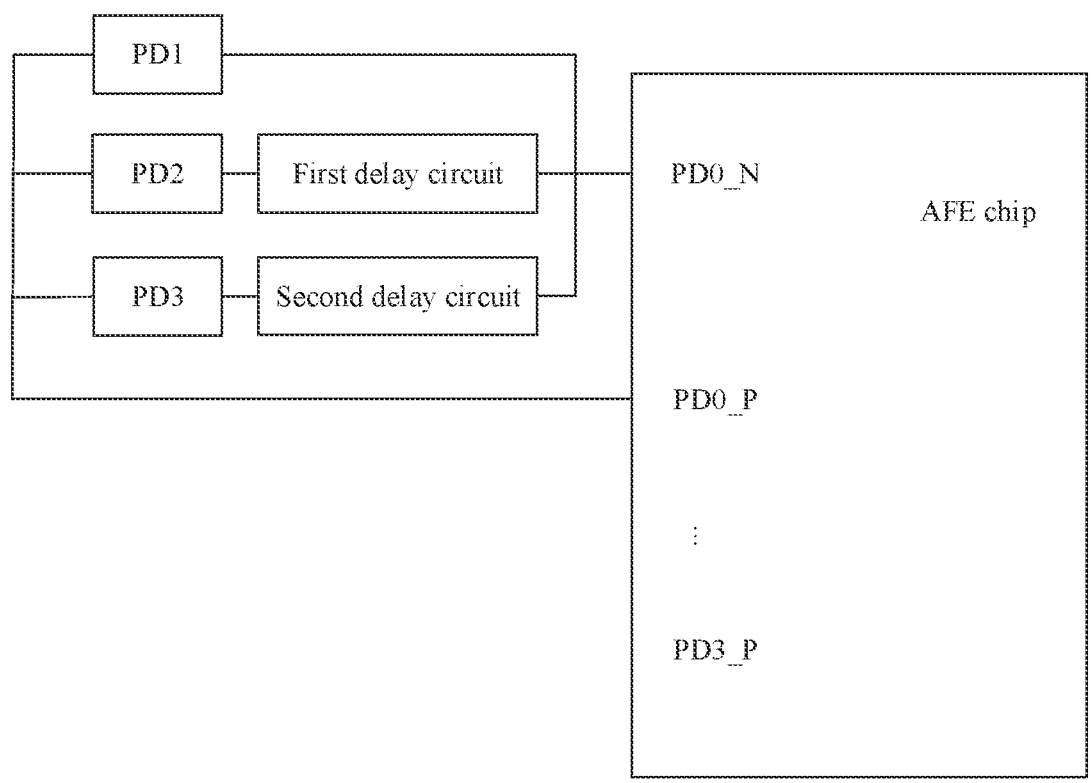
FIG. 8 is a schematic diagram of a structure of still another PD connection according to an embodiment of this application.

In addition, this embodiment is not limited to the structure in which two PDs are connected in parallel. In some possible implementations, three PDs may be connected in parallel, four PDs may be connected in parallel, or the like. With the delay circuit, multiple PDs connected in parallel may be received by the AFE chip through one receiving unit (RX). As shown in FIG. 8, the PD1, the PD2 and the PD3 are connected in parallel, the branch where the PD2 is located includes a first delay circuit, and the branch where the PD3 is located includes a second delay circuit. The first delay circuit may delay for T1, and the second delay circuit may delay for T2. The RX receives the signal of the PD1 at t0 to t1, receives the signal of the PD2 at (t0+T1) to (t1+T1), and receives the signal of the PD3 at (t0+T2) to (t1+T2). T2 may be equal to 2T1.

Figure 9:
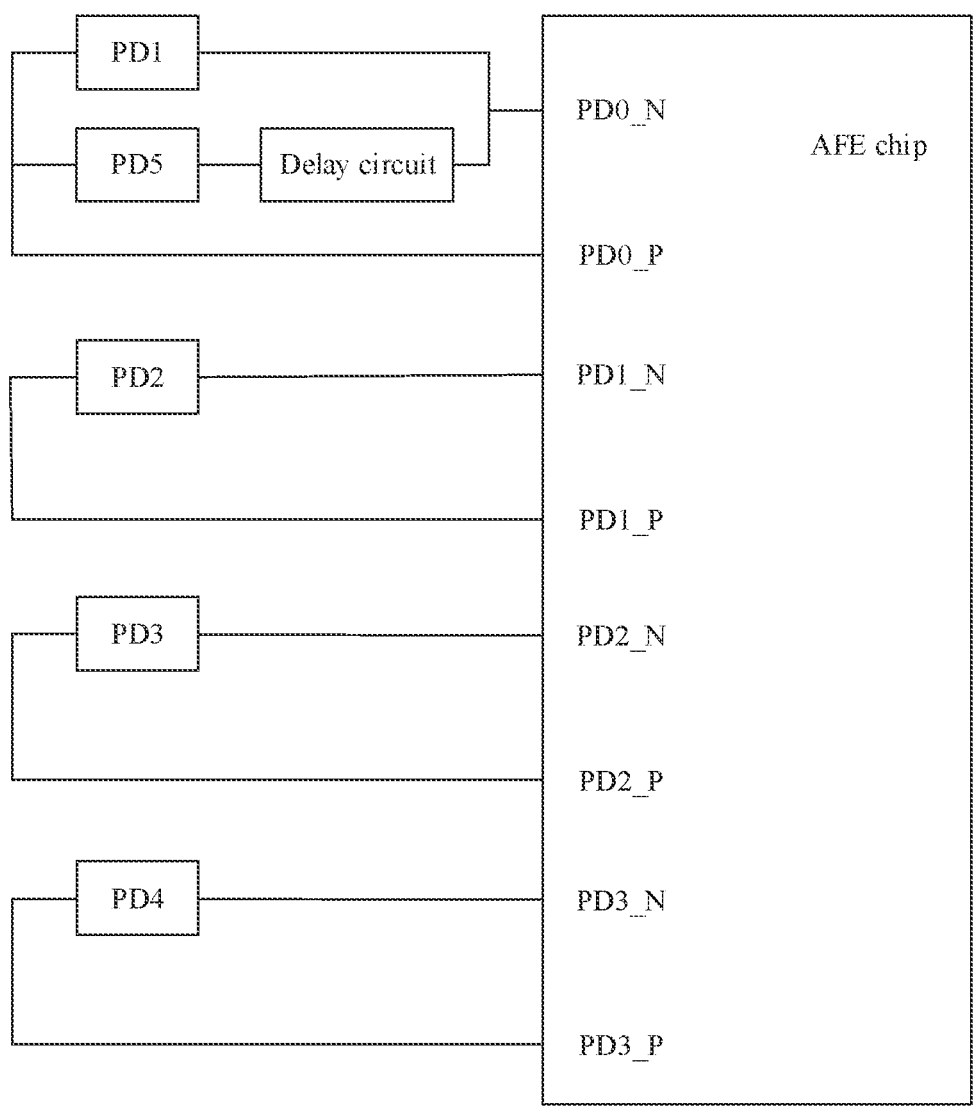
FIG. 9 is a schematic diagram of a structure of yet another PD connection according to an embodiment of this application.

Further, the method of adding a delay circuit in parallel branches in this embodiment is not limited to enabling the AFE chip with four receiving units to obtain more than four signals. When the chip applied in this scenario is a chip with n receiving units, this embodiment is still applicable to obtaining more than n signals. In addition, when the AFE chip has four receiving units, this embodiment is not limited to the obtaining of eight signals and twelve signals. When five signals need to be obtained, two of the PDs may be connected to the chip in parallel, and the remaining PDs are connected to the chip normally, as shown in FIG. 9.

That the PD1 and the PD2 are connected in parallel, and a delay circuit is added to the branch where the PD2 is located is used as an example below to describe the delay circuit in this embodiment. The RX0 receives a signal collected by the PD1 and, after delay time T, receives a signal collected by the PD2, so that signals collected by different PDs at t0 to t1 may be independently obtained. The AFE chip may send independent PD1 signal and PD2 signal into the FIFO, and evaluate the signal quality based on a channel selection algorithm, so as to obtain a target signal.

Figure 10:
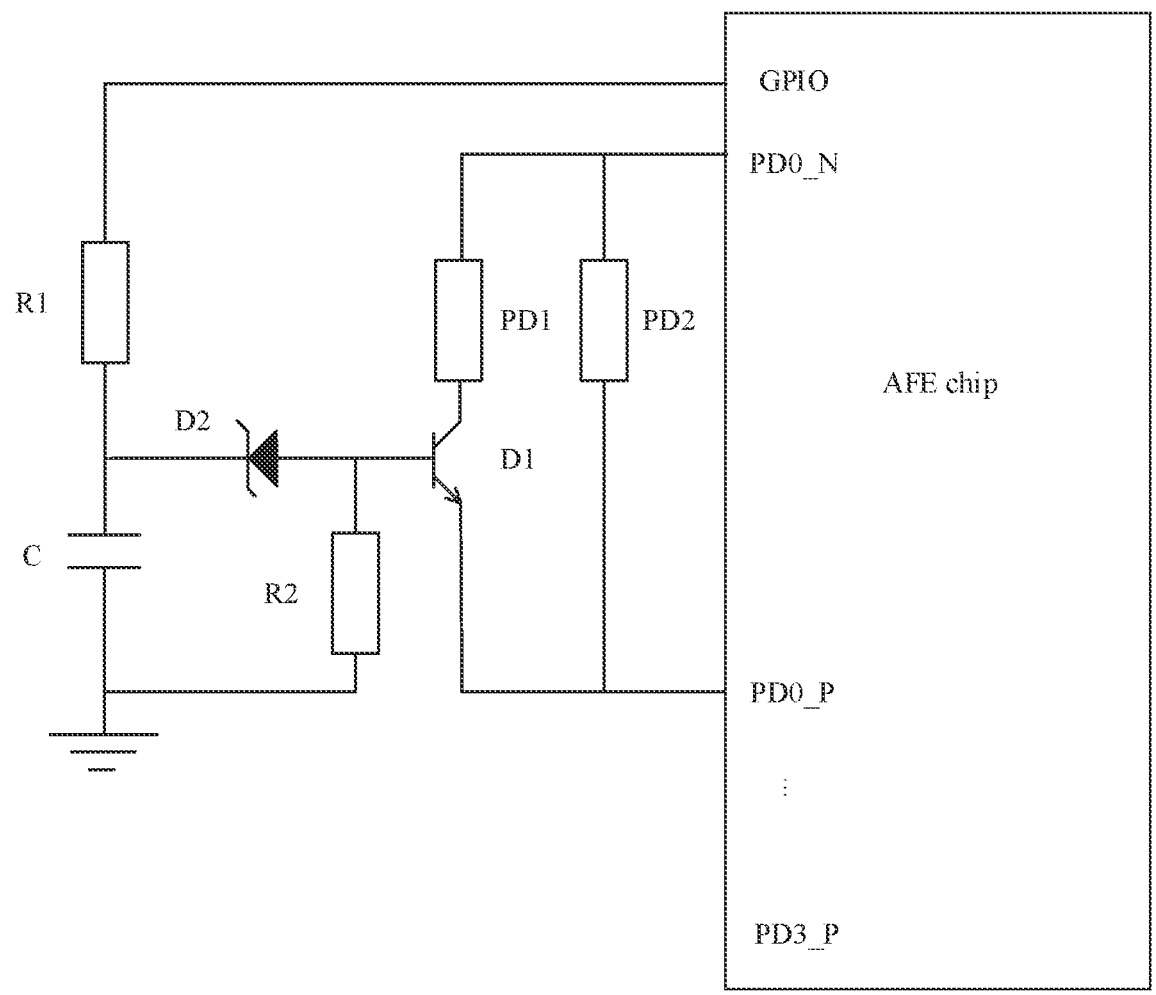
FIG. 10 is a schematic diagram of a structure of another delay circuit according to an embodiment of this application.

FIG. 10 shows an example of a delay circuit. The delay circuit includes an RC filter and a controllable switching transistor, where the controllable switching transistor may be a bipolar junction transistor (bipolar junction transistor, BJT) or a metal-oxide semiconductor field effect transistor (metal-oxide semiconductor field effect transistor, MOSFET). The RC filter includes a resistor and a capacitor. In this embodiment, that the controllable switching transistor is an NPN triode is used as an example for description. A control end (a base of the NPN triode in this embodiment) of an NPN triode D1 is connected to a first end of a resistor R1 and a first end of a capacitor C, a first end (a collector of the NPN triode in this embodiment) of the NPN triode D1 is connected to the first PD (the PD2 shown in the figure), a second end (an emitter) of the NPN triode is connected to an input end of the AFE chip, a second end of the resistor R1 is connected to a general-purpose interface (GPIO) of the AFE chip, and a second end of the capacitor C is grounded. The GPIO is a general-purpose input/output interface of the AFE chip. A first end of the PD2 is connected to a PD0_N pin of the AFE chip, the first end of the PD2 is connected to a collector of an N triode D1, and an emitter of the N triode D1 is connected to a PD0_P pin of the AFE chip. A first end of the PD1 is connected to the PD0_N pin of the AFE chip, and a second end of the PD1 is connected to the PD0_P pin of the AFE chip. The branch where the PD2 and the delay circuit are located is connected in parallel to the branch where the PD1 is located, and connected to the AFE chip through the PD0_N pin and the PD0_P pin of the AFE chip.

The RC filter including the resistor R1 and the capacitor C is configured to control voltage at the base of the NPN triode, and the NPN triode is configured to turn on when the voltage at the base is higher than a preset threshold, so as to implement the delay processing of the first electrical signal. Further, the delay circuit may also include a diode D2 and a voltage stabilizing resistor R2, which are used for voltage stabilization.

In actual application, resistance of the resistor R1 and capacitance of the capacitor C may be determined based on required delay time T. Therefore, the RC filter may control the NPN triode to turn on after time T delayed by the delay circuit. Therefore, the electrical signal of the PD2 enters the AFE chip after T, and the AFE chip may obtain, at different time, electrical signals generated by the PD1 and the PD2 at the same time.

Figure 11:
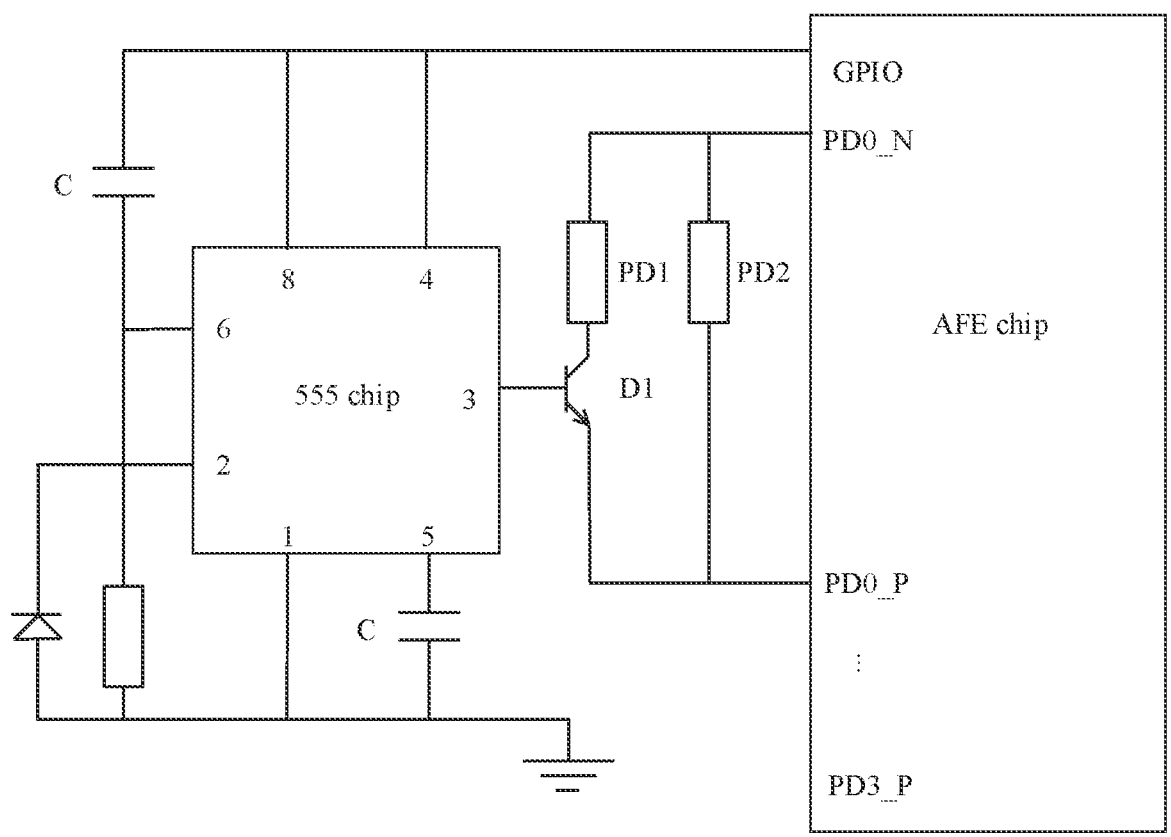
FIG. 11 is a schematic diagram of a structure of still another delay circuit according to an embodiment of this application.

FIG. 11 shows an example of another delay circuit. The delay circuit includes a timer and a controllable switching transistor, where the timer may be any chip that can achieve timer effect, and the controllable switching transistor may be a BJT or an MOSFET. In this embodiment, for example, the timer is a 555 chip, and the controllable switching transistor is an NPN triode. A control end (base) of the NPN triode is connected to an output end (pin 3) of the 555 chip, a first end (collector) of the NPN triode is connected to the first PD (the PD2), and a second end (emitter) of the NPN triode is connected to an input end of the AFE chip. Further, the delay circuit also includes a resistor R, a capacitor C1, a capacitor C2, and a diode D2. Specifically, a pin 1 of the 555 chip is grounded, a pin 2 is connected to a pin 6, and connected to a first end of the capacitor C1, a negative electrode of the diode D2 and a first end of the resistor R, and a second end of the resistor R is connected to a positive electrode of the diode and is grounded. The pin 2 and the pin 6 of the 555 chip are configured to determine whether the timer is turned on at a low level or a high level. The pin 3 is connected to the base of the NPN triode D1, the collector of the NPN triode D1 is connected to the second end of the PD2, and the emitter is connected to the PD0_P pin of the AFE chip. A pin 4 and a pin 8 are connected to a GPIO pin of the AFE chip and the second end of the capacitor C1. A pin 5 is connected to a first end of the capacitor C2, and a second end of the capacitor C2 is connected to the pin 1, the second end of the resistor R, and a positive electrode of the diode D2, and is grounded. The second end of the PD2 is connected to the PD0_N pin of the AFE chip. The first end of the PD1 is connected to the PD0_N pin of the AFE chip, and a negative electrode is connected to the PD0_P pin of the AFE chip. The branch where the PD2 and the delay circuit are located is connected in parallel to the branch where the PD1 is located, and connected to the AFE chip through the PD0_N pin and the PD0_P pin of the AFE chip.

The 555 chip, as a timer, is configured to delay the first electrical signal output to the base of the NPN triode for a preset time T compared with the second electrical signal. The delay time may be controlled by setting the preset time T in the 555 chip.

When output voltage of the pin 3 of the 555 chip is higher than voltage across the base and the emitter of the NPN triode D1, the triode is turned on, and the electrical signal of the PD2 enters the AFE chip. Therefore, the electrical signal of the PD2 enters the AFE chip after T, and the AFE chip may obtain, at different time, electrical signals generated by the PD1 and the PD2 at the same time.

Figure 12:
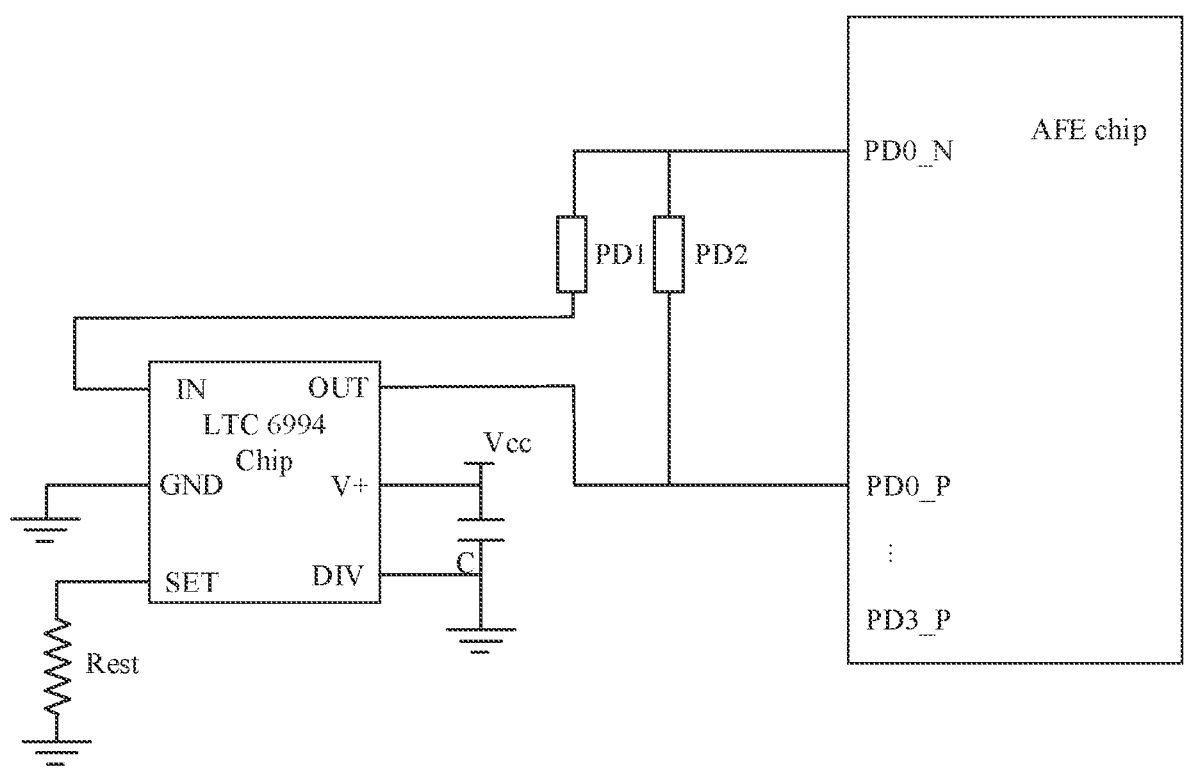
FIG. 12 is a schematic diagram of a structure of yet another delay circuit according to an embodiment of this application.

FIG. 12 shows an example of still another delay circuit. The delay circuit includes a power management chip, where the power management chip may be any chip that includes a signal input pin, a signal output pin, and a power input pin, and can achieve delay effect through direct current voltage. In this embodiment, for example, the power management chip is an LTC6994 chip, and the LTC6994 chip is connected in series with the first PD through the signal input pin and the signal output pin. The delay circuit further includes a capacitor C, a resistor REST, and an external power supply Vcc. Specifically, an IN pin of the LTC6994 chip is connected to the first end of the PD2, the second end of the PD2 is connected to the PD0_N pin of the AFE chip, a GND pin of the LTC6994 chip is grounded, an SET pin is connected to the resistor REST, a DIV pin is grounded and connected to the first end of the capacitor C, the second end of the capacitor C is connected to a V+ pin and the external power supply Vcc, and an OUT pin is connected to the PD0_P pin of the AFE chip. A positive electrode of the PD1 is connected to the PD0_N pin of the AFE chip, and a negative electrode is connected to the PD0_P pin of the AFE chip. The branch where the PD2 and the delay circuit are located is connected in parallel to the branch where the PD1 is located, and connected to the AFE chip through the PD0_N pin and the PD0_P pin of the AFE chip.

The power management chip is configured to generate, by using the direct current voltage, a first electrical signal delayed for a preset time compared with the second electrical signal. An IN end of the LTC6994 chip may receive input voltage of the PD2, and then output the input voltage to the AFE chip after the preset time T, so as to delay the electrical signal of the PD2. Therefore, the AFE chip may obtain, at different time, electrical signals generated by the PD1 and the PD2 at the same time.

Figure 13:
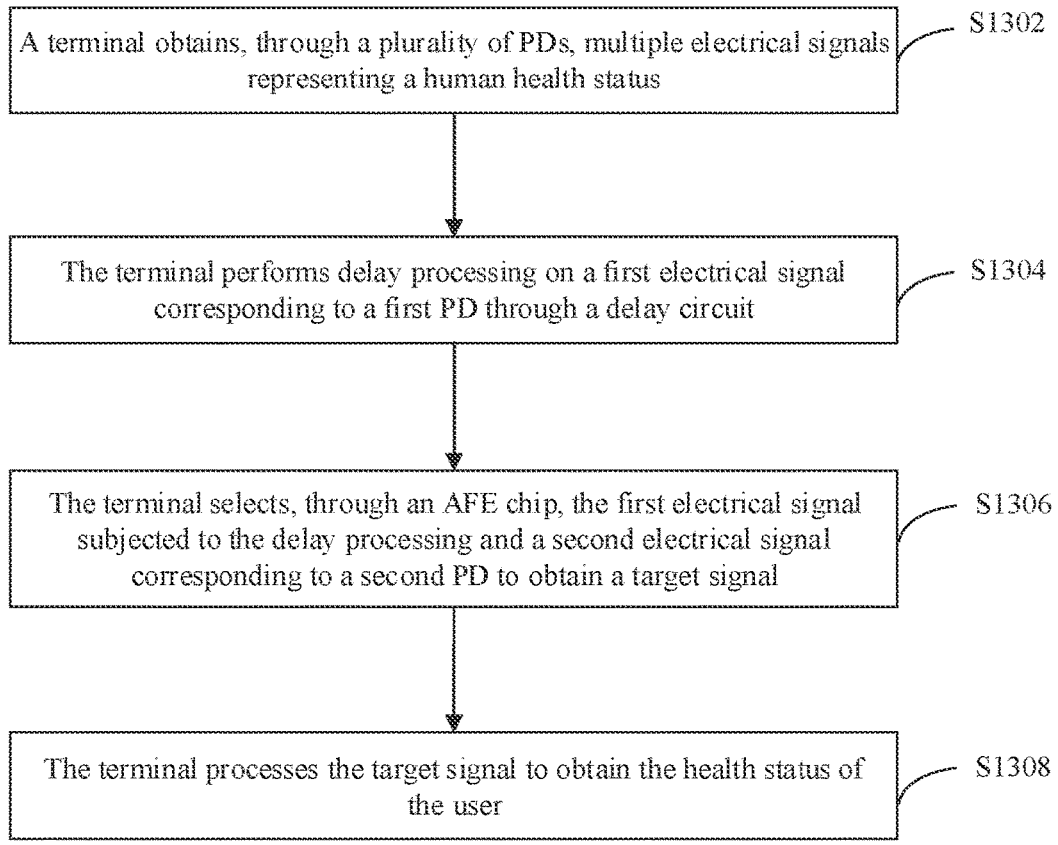
FIG. 13 is a schematic flowchart of a PPG control method according to an embodiment of this application.

An architecture of a PPG signal processing method has been briefly described above. Specific steps of a PPG signal processing method in this embodiment are described below with reference to FIG. 13.

S1302: The terminal obtains, through a plurality of PDs, multiple electrical signals representing a human health status.

The electrical signals are obtained by the PDs through photoelectric conversion based on received optical signals, where the optical signals refer to optical signals emitted by the LED and reflected by human skin. The absorption of light by human muscles, bones, and veins is essentially unchanged without substantial movement, while blood is flowing, so that the absorption of light is changing. Therefore, optical signals reflected by human skin can represent a human health status.

The plurality of PDs are in one-to-one correspondence with multiple electrical signals. The plurality of PDs receive the optical signals reflected by human skin, perform photoelectric conversion on the optical signals, and convert the optical signals into electrical signals to obtain an optical signal corresponding to each PD. Due to different positions of the plurality of PDs, different PDs obtain different optical signals.

In some possible implementations, to occupy an angle of the dial of the smartwatch as much as possible, the plurality of PDs may be arranged in a surrounding structure, as shown in FIG. 3, so that an optical signal may be received by at least one of the plurality of PDs, regardless of which angle of the dial is in close contact with the human body. Further, the plurality of PDs may be closely distributed at a plurality of angles around the LED (an included angle between adjacent PDs is close to 0) to ensure that the PDs can receive optical signals when the dial is in close contact with the human body at any angle.

S1304: The terminal performs delay processing on the first electrical signal corresponding to the first PD through the delay circuit.

The first PD is a PD among the plurality of PDs, and the electrical signal corresponding to the first PD is the first electrical signal. The plurality of PDs include a first PD and a second PD. The first PD may be one PD, such as the PD5 in FIG. 9, or a plurality of PDs, such as the PD5, the PD6, the PD7, and the PD8 in FIG. 7, or the PD2 and the PD3 in FIG. 8.

The delay circuit may be a circuit including a delay circuit, where the delay circuit may be a delay circuit including resistors R1 and R2, a capacitor C, a diode D2, and a triode D1 as shown in FIG. 10, or a delay circuit including a 555 chip, a resistor R, a capacitor C1, a capacitor C2, a diode D2, and an N triode D1 as shown in FIG. 11, or a delay circuit including an LTC6994 chip, a capacitor C, a resistor REST, an external power supply Vcc, and an N triode D1 as shown in FIG. 12. The delay time T of the delay circuit is longer than the lighting time of the LED and shorter than the sampling interval of the AFE chip.

S1306: The terminal selects, through the AFE chip, the first electrical signal subjected to the delay processing and the second electrical signal corresponding to the second PD to obtain a target signal.

The AFE chip is configured to determine a target signal from signals input by a plurality of sensors. In this embodiment, the AFE chip is configured to select a target signal from a plurality of electrical signals corresponding to the plurality of PDs. The first electrical signal is an electrical signal subjected to delay processing by the delay circuit, and the second electrical signal is an electrical signal without delay processing. When a quantity of receiving units of the AFE chip is less than a quantity of PDs, the AFE chip may obtain, at different time, electrical signals collected at the same time by performing delay processing on the first electrical signal.

For example, when the AFE chip has four receiving units and eight PDs, as shown in FIG. 4, the PD2, the PD4, the PD6, and the PD8 are connected, through the delay circuit, in parallel to the connection of the PD1, the PD3, the PD5, and the PD7 to the AFE chip.

For example, the four receiving units of the AFE chip are RX0, RX1, RX2 and RX3, the LED emits light at t0 to t1, and delay time of the delay circuit is T. The RX0 receives a signal of the PD1 at t0 to t1, and receives a signal of the PD2 at (t0+T) to (t1+T); the RX1 receives a signal of the PD3 at t0 to t1, and receives a signal of the PD4 at (t0+T) to (t1+T); the RX2 receives a signal of the PD5 at t0 to t1, and receives a signal of the PD6 at (t0+T) to (t1+T); and the RX3 receives a signal of the PD7 at t0 to t1, and receives a signal of the PD8 at (t0+T) to (t1+T). Therefore, the AFE chip may collect eight PD signals independently.

The terminal may obtain, through the AFE chip, independent electrical signals collected by all PDs at the same time. Further, the terminal may evaluate the quality of multiple PD signals collected at the same time and obtained at different time based on a channel selection algorithm to obtain a target signal.

When evaluating the quality of the electrical signals corresponding to the plurality of PDs based on the channel selection algorithm, the terminal may evaluate the signal quality based on amplitude, images, and frequency domain energy of the signals. For example, it may be required that the DC signal amplitude of the signals is at a μA level, the AD signal amplitude is about 0.5% to 2% of the DC signal amplitude, the signals are free from obvious amplitude fluctuation and signal burr, and the frequency domain energy of the signals is concentrated at 0.5 Hz to 4 Hz.

S1308: The terminal processes the target signal to obtain a health status of the user.

The health status of the user may include at least one of heart rate status, blood oxygen status, and respiratory status of the user. The terminal may convert optical signals reflected by skin of the user into electrical signals to obtain corresponding features of the user. In some possible implementations, differences in wavelength, intensity, and frequency of light emitted by the LED correspond to different features representing a human health status. Further, the LED may also emit optical signals of different colors at the same time, so as to obtain, at the same time, a plurality of features representing a human health status.

In conclusion, this embodiment provides a signal processing method based on PPG. The terminal obtains, through the plurality of PDs, multiple electrical signals including human health data, where the multiple electrical signals correspond to the plurality of PDs one by one, the electrical signals are converted by the PDs based on received optical signals, and the optical signals are optical signals emitted by the LED and reflected by human skin, including a human health status. The terminal performs delay processing on the first electrical signal corresponding to the first PD through the delay circuit, so that the terminal may select, through the AFE chip, the electrical signal subjected to the delay processing and corresponding to the first PD and the second electrical signal corresponding to the second PD to obtain the target signal that can represent a human health status, and then analyze and process the target signal to obtain the human health status of the user. Therefore, the terminal performs, through the delay circuit, delay processing on the electrical signal corresponding to the first PD, which enables the electrical signals collected by the plurality of PDs to be independently received by the AFE chip, so that the AFE chip can select based on the electrical signal collected by each PD to obtain a target signal, so as to comprehensively extract target signals, avoid interference caused by signal superposition, and accurately determine the human health status of the user.

Figure 14:
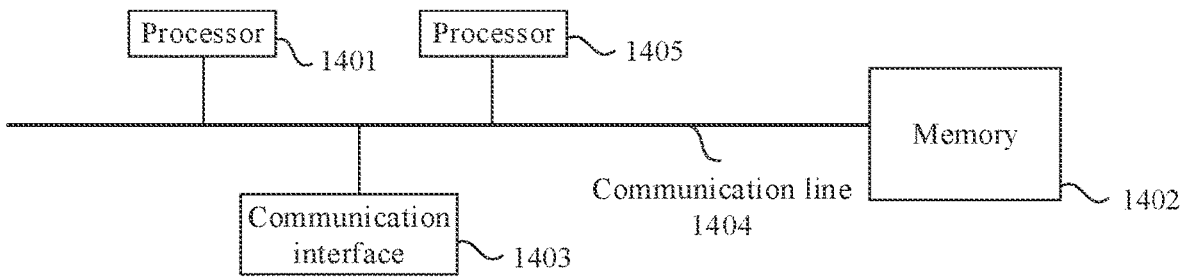
FIG. 14 is a schematic diagram of a hardware structure of a control device according to an embodiment of this application.

For example, FIG. 14 is a schematic diagram of a hardware structure of a control device according to an embodiment of this application. As shown in FIG. 14, the control device includes a processor 1401, a communication line 1404, and at least one communication interface (for example, in FIG. 14, a communication interface 1403 is used as an example for description).

The processor 1401 may be a general-purpose central processing unit (central processing unit, CPU), a microprocessor, an application-specific integrated circuit (application-specific integrated circuit, ASIC), or one or more integrated circuits for controlling program execution in the solutions of this application.

The communication line 1404 may include a circuit for transmitting information among the foregoing components.

The communication interface 1403, using any device such as a transceiver, is configured to communicate with other devices or communication networks, such as Ethernet, and a wireless local area network (wireless local area network WLAN).

Possibly, the control device may further include a memory 1402.

The memory 1402 may be a read-only memory (read-only memory, ROM) or another type of static storage device capable of storing static information and instructions, a random access memory (random access memory, RAM) or another type of dynamic storage device capable of storing information and instructions, or an electrically erasable programmable read-only memory (electrically erasable programmable read-only memory, EEPROM), a compact disc read-only memory (compact disc read-only memory, CD-ROM) or another optical disc memory, a compact disc memory (including a compact disc, a laser disc, an optical disc, a digital versatile discs, a Blu-ray disc, and the like), magnetic disc storage medium or another magnetic storage device, or any other medium that can be used to carry or store desired program code in the form of instructions or data structures and that can be accessed by a computer, but is not limited thereto. The memory may be stand-alone and connected to the processor through the communication line 1404. The memory may alternatively be integrated with the processor.

The memory 1402 is configured to store computer-executable instructions for executing the solutions in this application under control of the processor 1401. The processor 1401 is configured to execute computer-executable instructions stored in the memory 1402 to implement the control method according to the embodiments of this application.

Possibly, the computer-executable instructions in this embodiment of this application may alternatively be referred to as application code, which is not specifically limited in this embodiment of this application.

During specific implementation, in an embodiment, the processor 1401 may include one or more CPUs, such as a CPU0 and a CPU1 in FIG. 14.

During specific implementation, in an embodiment, the control device may include a plurality of processors, such as a processor 1401 and a processor 1405 in FIG. 14. Each of these processors may be a single-core (single-CPU) processor or a multi-core (multi-CPU) processor. The processor herein may refer to one or more devices, circuits, and/or processing cores for processing data (such as computer program instructions).

In the foregoing embodiments, the instructions stored in the memory for execution by the processor may be implemented in the form of a computer program product. The computer program product may be written in the memory in advance, or may be downloaded and installed in the memory in the form of software.

The computer program product includes one or more computer instructions. When the computer program instructions are loaded and executed on the computer, the procedure or functions according to embodiments of this application are completely or partially generated. The computer may be a general-purpose computer, a special-purpose computer, a computer network, or another programmable apparatus. The computer instructions may be stored in a computer readable storage medium or transmitted from one computer readable storage medium to another computer readable storage medium. For example, the computer instructions may be transmitted from one network site, computer, server or data center to another network site, computer, server or data center in a wired (such as coaxial cable, optical fiber, or digital subscriber line (DSL)) or wireless (such as infrared, wireless, or microwave) manner. The computer-readable storage medium may be any available medium accessible by a computer, or a data storage device such as a server or a data center, integrating one or more available media. For example, the available medium may include a magnetic medium (for example, a floppy disk, a hard disk, or a magnetic tape), an optical medium (for example, a digital versatile disc (digital versatile disc, DVD)), or a semiconductor medium (for example, a solid state disk (solid state disk, SSD)).

An embodiment of this application further provides a computer readable storage medium. All or some of the methods described in embodiments may be implemented by software, hardware, firmware, or any combination thereof. The computer-readable medium may include a computer storage medium and a communication medium, and may alternatively include any medium that may transmit a computer program from one place to another. The storage medium may be any target medium accessible by the computer.

In a possible design, the computer-readable medium may include a compact disc read-only memory (compact disc read-only memory, CD-ROM), a RAM, a ROM, an EEPROM, or another optical disc memory; and the computer-readable medium may include a magnetic disc memory or another disk storage device. In addition, any connecting line may be appropriately referred to as a computer-readable medium. For example, if software is transmitted from a website, a server or another remote source by using a coaxial cable, an optical fiber cable, a twisted pair, a DSL or wireless technologies (for example, infrared, radio, and microwave), the coaxial cable, the optical fiber cable, the twisted pair, the DSL or wireless technologies such as infrared, radio and microwave are included in the definition of medium. As used herein, magnetic and optical discs include a compact disc (CD), a laser disc, an optical disc, a digital versatile disc (digital versatile disc, DVD), a floppy disc, and a Blu-ray disc, and the magnetic disc usually reproduces data magnetically, while the optical disc reproduces data optically using lasers.

The foregoing combinations should also be included in the scope of the computer-readable medium. The foregoing descriptions are merely specific implementations of the present invention, but are not intended to limit the protection scope of the present invention. Any variation or replacement readily figured out by a person skilled in the art within the technical scope disclosed in the present invention shall fall within the protection scope of the present invention. Therefore, the protection scope of the present invention shall be subject to the protection scope of the claims.

What is claimed is:

1. A terminal based on photo plethysmo graph PPG, comprising a light emitting diode LED, an analog front end AFE chip, a processor, and a plurality of photo diodes PDs, wherein the plurality of photo diodes PDs comprise a first PD and a second PD, the first PD and the second PD are connected to the AFE chip in parallel, and the AFE chip is connected to the processor;
   the LED is configured to emit a first optical signal to the skin of a user;
   the first PD is configured to receive a second optical signal reflected by the skin of the user, and convert the second optical signal into a first electrical signal;
   the second PD is configured to receive the second optical signal reflected by the skin of the user, and convert the second optical signal into a second electrical signal; wherein
   the terminal further comprises a delay circuit, and the delay circuit is connected in series in a branch where the first PD is located;
   the delay circuit is configured to perform delay processing on the first electrical signal;
   the AFE chip is configured to determine a target signal based on the second electrical signal and the first electrical signal subjected to the delay processing; and
   the processor is configured to process the target signal to obtain a health status of the user.

2. The terminal according to claim 1, wherein the delay circuit comprises an RC filter and a controllable switching transistor, and the RC filter comprises a resistor and a capacitor;
   a control end of the controllable switching transistor is connected to a first end of the resistor and a first end of the capacitor, a first end of the controllable switching transistor is connected to the first PD, a second end of the controllable switching transistor is connected to an input end of the AFE chip, a second end of the resistor is connected to a general-purpose interface of the AFE chip, and a second end of the capacitor is grounded;
   the RC filter is configured to control voltage at the control end of the controllable switching transistor; and
   the controllable switching transistor is configured to turn on when the voltage at the control end is higher than a preset threshold, so as to perform delay processing on the first electrical signal.

3. The terminal according to claim 1, wherein the delay circuit comprises a timer and a controllable switching transistor;
   a control end of the controllable switching transistor is connected to an output end of the timer, a first end of the controllable switching transistor is connected to the first PD, and a second end of the controllable switching transistor is connected to an input end of the AFE chip; and
   the timer is configured to delay the first electrical signal output to the control end of the controllable switching transistor for a preset time compared with the second electrical signal.

4. The terminal according to claim 1, wherein the delay circuit comprises a power management chip;
   the power management chip comprises a signal input pin, a signal output pin, and a power input pin, wherein the power input pin is configured to connect to a direct current voltage, and the power management chip is connected to the first PD in series through the signal input pin and the signal output pin; and
   the power management chip is configured to generate, by using the direct current voltage, a first electrical signal delayed for a preset time compared with the second electrical signal.

5. The terminal according to claim 1, wherein the plurality of PDs are eight PDs, the first electrical signal is four electrical signals generated by four of the eight PDs, and the AFE chip has four signal receiving channels.

6. The terminal according to claim 1, wherein the plurality of PDs are twelve PDs, the first PD comprises four first sub-PDs and four second sub-PDs, the AFE chip has four signal receiving channels, and the first sub-PDs and the second sub-PDs are connected to the AFE chip in parallel;
   the first sub-PDs are configured to receive a second optical signal reflected by the skin of the user, and convert the second optical signal into a first sub-electrical signal;
   the second sub-PDs are configured to receive the second optical signal reflected by the skin of the user, and convert the second optical signal into a second sub-electrical signal;
   the delay circuit comprises a first delay circuit and a second delay circuit, the first delay circuit and the second delay circuit have different delay time, the first delay circuit is connected in series in a branch where the first sub-PDs are located, and the second delay circuit is connected in series in a branch where the second sub-PDs are located;
   the first delay circuit is configured to perform delay processing on the first sub-electrical signal; and
   the second delay circuit is configured to perform delay processing on the second sub-electrical signal.

7. The terminal according to claim 1, wherein the plurality of PDs are annularly distributed.

8. The terminal according to claim 1, wherein the health status of the user comprises at least one of heart rate, oxygen saturation, and respiratory rate of the user.

9. The terminal according to claim 1, wherein the terminal is a wearable device.

10. The terminal according to claim 1, wherein the first optical signal is at least one of a red light signal, a green light signal, and an infrared light signal.

\* \* \* \* \*